United States Patent [19]

Noso et al.

[11] Patent Number: 4,989,973
[45] Date of Patent: Feb. 5, 1991

[54] SURFACE CONDITION ESTIMATING APPARATUS

[75] Inventors: Kazunori Noso, Yokohama; Hiroshi Saito, Yokosuka, both of Japan

[73] Assignee: Nissan Motor Co., Ltd., Japan

[21] Appl. No.: 415,582

[22] Filed: Oct. 2, 1989

[30] Foreign Application Priority Data

Oct. 3, 1988 [JP] Japan .............................. 63-247434
Oct. 12, 1988 [JP] Japan .............................. 63-254902

[51] Int. Cl.$^5$ .................... G01B 11/00; G06K 9/00; G01N 21/84
[52] U.S. Cl. .................................... 356/239; 382/55
[58] Field of Search ................... 356/237, 239; 382/55

[56] References Cited

U.S. PATENT DOCUMENTS

| | | | |
|---|---|---|---|
| 4,002,823 | 1/1977 | Van Oosterhout | 356/239 |
| 4,449,818 | 5/1984 | Yamaguchi et al. | 356/237 |
| 4,468,120 | 8/1984 | Tanimoto et al. | 356/237 |
| 4,889,998 | 12/1989 | Hayano et al. | 356/237 |

OTHER PUBLICATIONS

Rapa et al., "Sequencing Oblique Light" *IBM Technical Disclosure Bulletin* vol. 22, No. 6, (Nov. 1979), pp. 2284–2285.

*Primary Examiner*—Richard A. Rosenberger
*Attorney, Agent, or Firm*—Leydit, Voit & Mayer

[57] ABSTRACT

An apparatus for estimating a surface condition of a plate object. The apparatus comprises a lighting unit for generating light toward the plate object. A light sensor is located out of paths of the light generated from the lighting unit for producing an electrical signal in response to light of diffused reflection from the plate object. The apparatus also includes a processing unit for processing the electrical signal fed thereto from the light sensor for producing an image including a defective portion reflective of the light of diffused reflection, and an estimating unit for estimating the surface condition of the plate object based on the defective portion of the produced image. In another aspect of the invention, the apparatus comprises a lighting unit for generating light toward the plate object. A light sensor is provided for converting brightness variations of the light impinging on the plate object into an electrical signal. The apparatus also includes a processing unit for processing the electrical signal fed thereto from the light sensor for producing a plurality of image segments forming a full image of the surface of the plate object, and an estimating unit for estimating the surface condition of the plate object based on a defective portion included in each of the image segments. The estimating unit includes means for providing a heavier weight on a defective portion of at least one of the image segments than that of the other image segments.

19 Claims, 13 Drawing Sheets

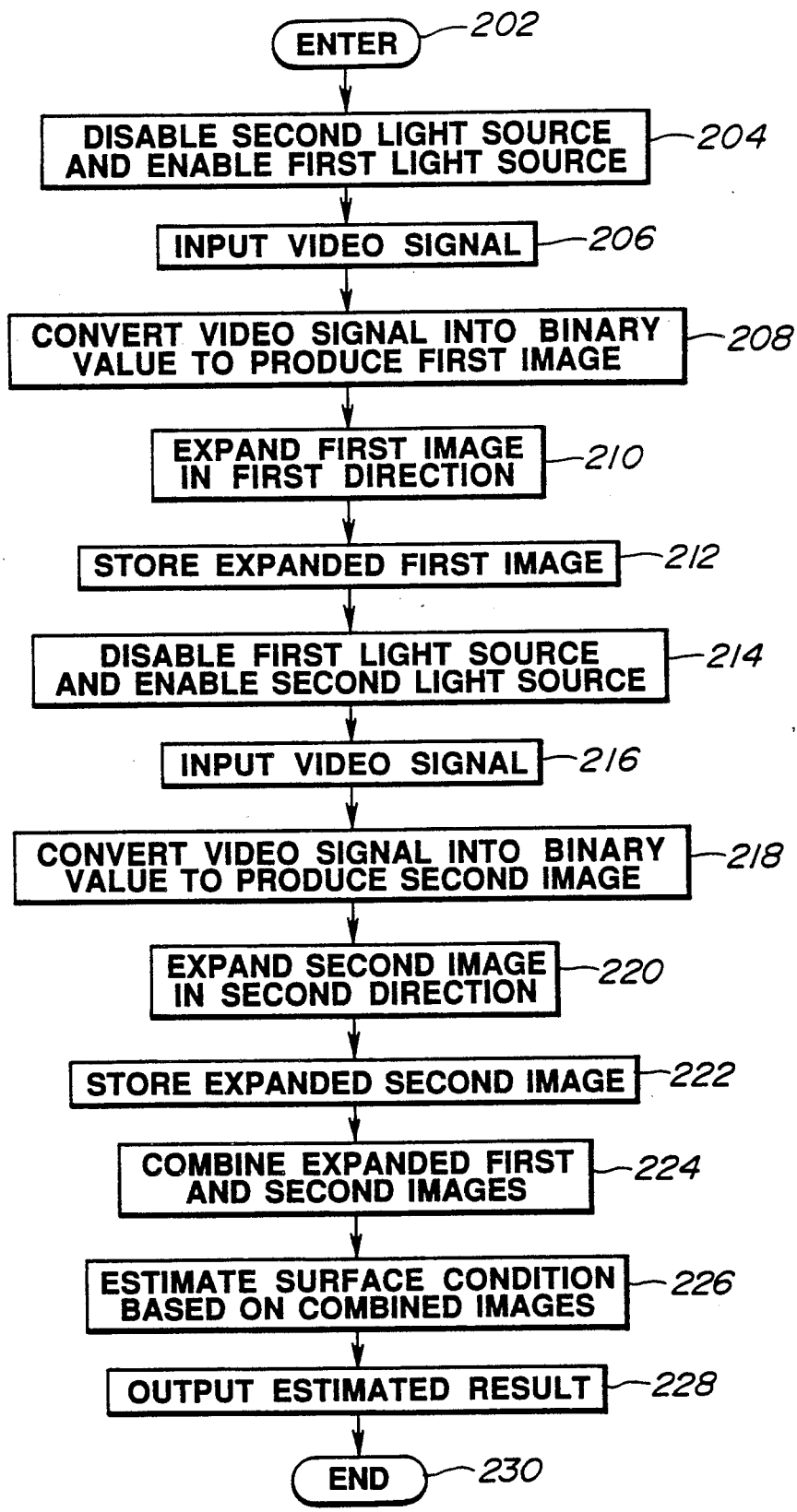

FIG. 5

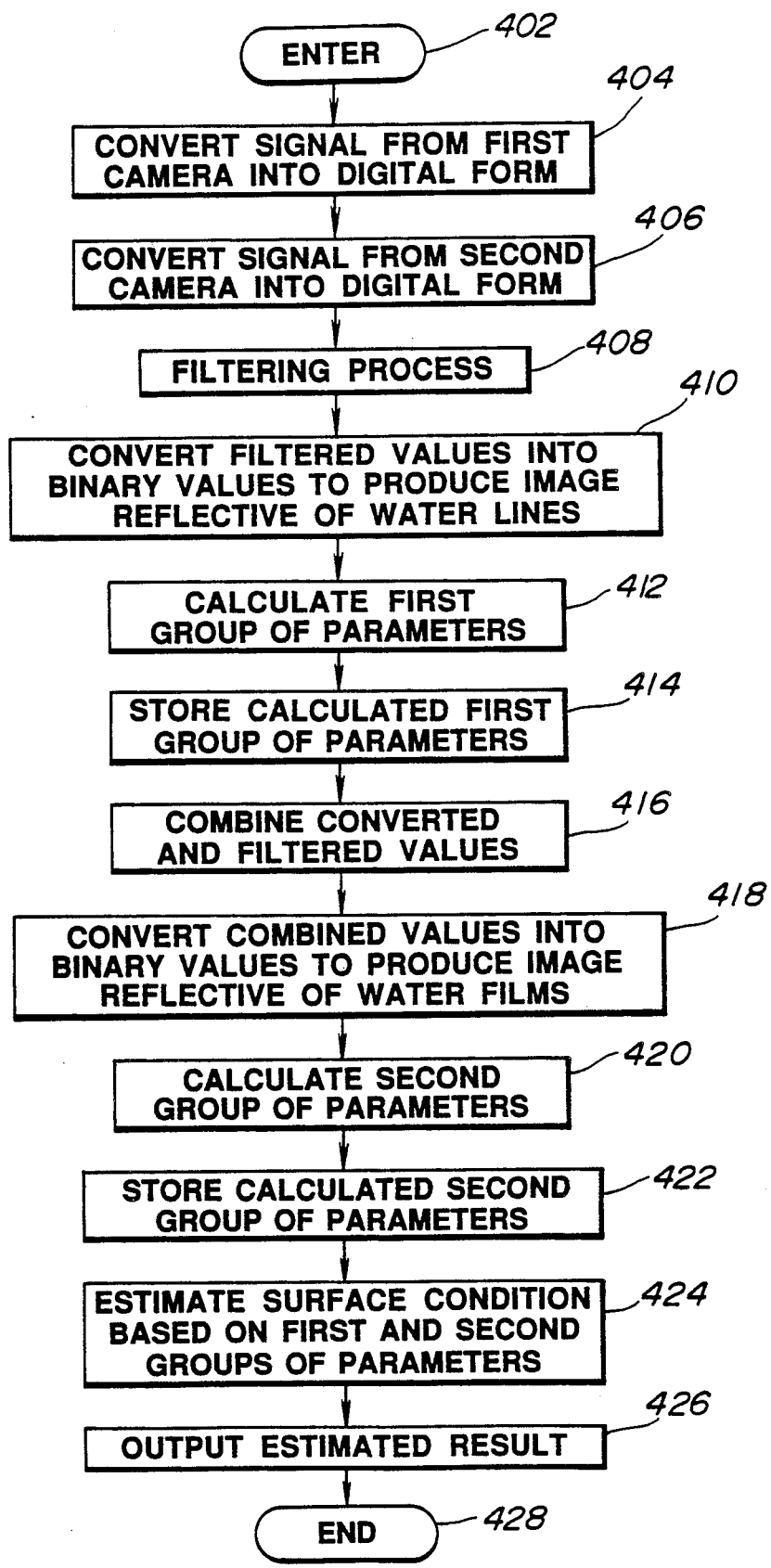

SURFACE CONDITION ESTIMATING APPARATUS

BACKGROUND OF THE INVENTION

This invention relates to an apparatus employing a dioptric or catoptric optical system for estimating the surface condition of a plate object to be tested. The term "surface condition" as used throughout this invention is intended to mean the degree of scratches, streaks, moisture, water droplets, water lines, water films, stains, and the like collected or left on the surface(s) of the plate object.

It is the current practice to estimate the surface condition of the plate object with the eye. Therefore, the estimation accuracy is dependent on the inspector's skill and is different from one inspector to another.

SUMMARY OF THE INVENTION

It is a main object of the invention to provide a surface condition estimating apparatus which can ensure reliable and rapid estimation of the surface condition of plate objects.

There is provided, in accordance with the invention, an apparatus for estimating a surface condition of a plate object. The apparatus comprises a lighting unit for generating light toward the plate object. A light sensor is located out of paths of the light generated from the lighting unit for producing an electrical signal in response to light of diffused reflection from the plate object. The apparatus also comprises a processing unit for processing the electrical signal fed thereto from the light sensor for producing an image including a defective portion reflective of the light of diffused reflection, and an estimating unit for estimating the surface condition of the plate object based on the defective portion of the produced image.

In another aspect of the invention, there is provided an apparatus for estimating a surface condition of a plate object. The apparatus comprises a lighting unit for generating light toward the plate object. A light sensor is provided for converting brightness variations of the light impinging on the plate object into an electrical signal. The apparatus also comprises a processing unit for processing the electrical signal fed thereto from the light sensor for producing a plurality of image segments forming a full image of the surface of the plate object, and an estimating unit for estimating the surface condition of the plate object based on a defective portion included in each of the image segments. The estimating unit includes means for providing a heavier weight on a defective portion of at least one of the image segments than that of the other image segments.

In still another aspect of the invention, there is provided an apparatus for estimating an efficiency of a wind-shield wiper provided for wiping a surface of a wind-shield glass plate. The apparatus comprises a lighting unit for generating light toward the wind-shield glass plate. A light sensor is provided for converting brightness variations of the light impinging on the wind-shield glass plate into an electrical signal. The apparatus also comprises a processing unit for processing the electrical signal fed thereto from the light sensor for producing a plurality of image segments forming a full image of the surface of the wind-shield glass plate, and an estimating unit for estimating the efficiency of the wind-shield wiper based on a defective portion included in each of the image segments. The estimating unit includes means for providing a heavier weight on a defective portion of at least one of the image segments than that of the other image segments.

BRIEF DESCRIPTION OF THE DRAWINGS

This invention will be described in greater detail by reference to the following description taken in connection with the accompanying drawings, in which:

FIG. 3 is a flow diagram of the programming of the digital computer used in the apparatus of FIG. 1;

FIG. 5 is a diagram used in explaining the masking operation of the image processing unit;

FIG. 16 is a flow diagram of the programming of the digital computer used in the apparatus of FIG. 14;

DETAILED DESCRIPTION OF THE INVENTION

Figure 1:
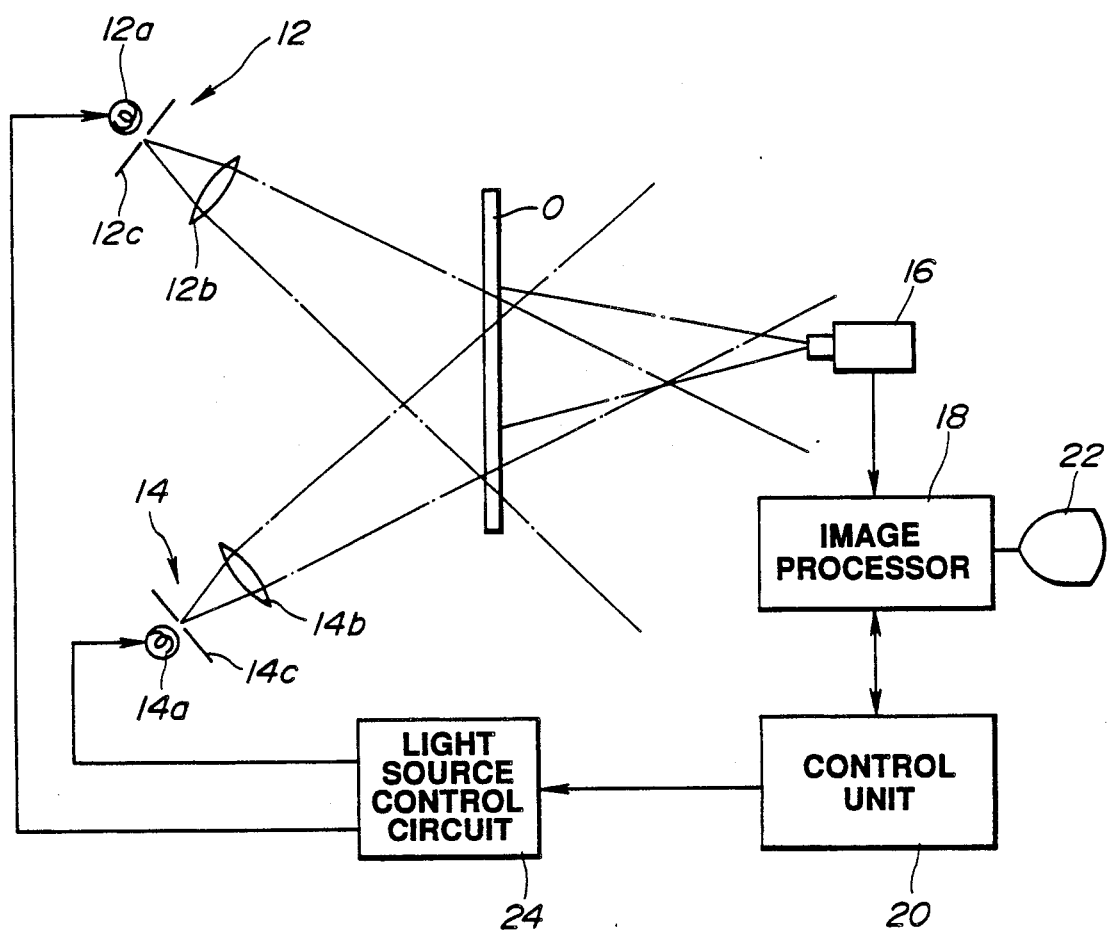
FIG. 1 is a schematic diagram showing one embodiment of a surface condition estimating apparatus made in accordance with the invention.

With reference to the drawings, wherein like numerals refer to like parts in the several views, and in particular to FIG. 1, there is shown a schematic diagram of a surface condition estimating apparatus embodying the method and apparatus of the invention. In the embodiment of FIG. 1, a transparent plate object O, for example, a gloss plate or the like having opposite smooth surfaces, is tested for estimation of the surface condition thereof.

A lighting unit 10, positioned on one side of the transparent plate object O, includes a plurality of (in the illustrated case two) separate light sources 12 and 14 for generating light beams travelling in different directions toward one side surface of the transparent plate object O. The first light source 12 comprises a lamp 12a, a lens 12b, and an aperture diaphragm 12c located between the lamp 12a and the lens 12b. Preferably, the aperture diaphragm 12c is located at the focal point of the lens 12b so as to collimate the light directed toward the transparent plate object O. Similarly, the second light source 14 comprises a lamp 14a, a lens 14b, and an aperture diaphragm 14c located between the lamp 14a and the lens 14b. It is preferable to locate the aperture diaphragm 14c at the focal point of the lens 14b so as to collimate the light directed toward the transparent plate object O. The light generated from the first and second light sources 12 and 14 passes through the transparent object O.

A light sensor taken in the form of a television camera 16 is shown as located on the other side of the transparent plate object O remote from the lighting unit 10 and out of the optical paths of the light passing through the transparent plate object O so that the camera can receive light of diffused reflection on the transparent plate object O. The camera 15 is focused on the transparent plate object O.

Figure 2:
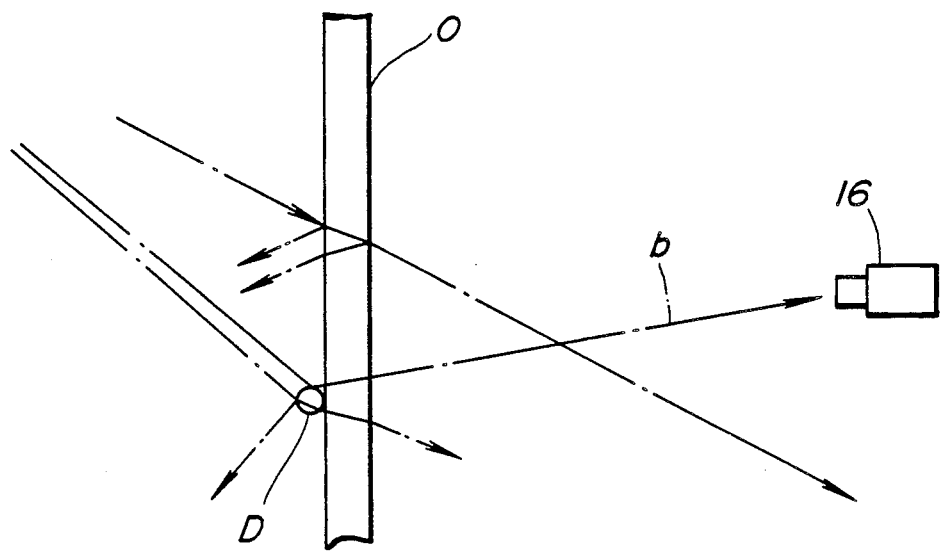
FIGS. 2A, 2B and 2C are diagrams used in explaining the light of diffused reflection from the transparent plate object.
Figure 2:
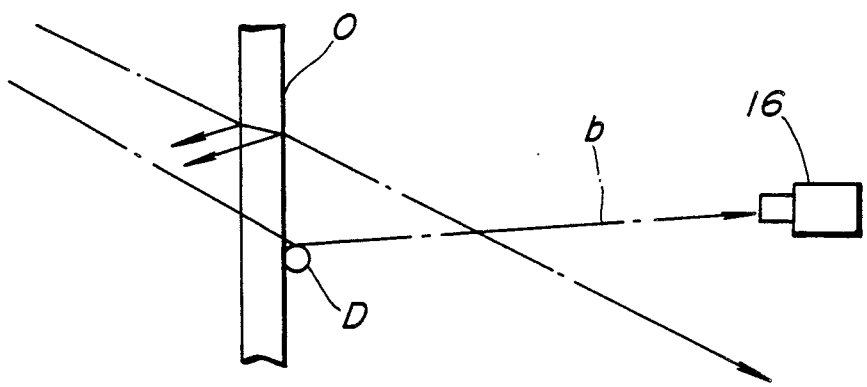
Figure 2:
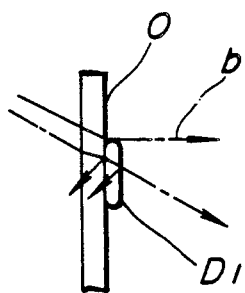

The light generated from the first and second light sources 12 and 14 passes through the transparent plate object O. When the transparent plate object O is complete, the camera 16 receives no light, as shown in FIG. 1. Assuming now that a water droplet D exists on either of the opposite surfaces of the transparent plate object O, as shown in FIGS. 2A and 2B, the camera 16 receives the light of diffused reflection on the water droplet D, as indicated by the phantom lines b of FIGS. 2A and 2B. It is preferable to alternatively actuate the first and second light sources 12 and 14 in order to provide an accurate estimation for a relatively large water droplet. The reason for this is that the light tends to reflect mainly on the circumference of the large water droplet D1, as shown in FIG. 2D.

The camera 16 produces a video signal which is coupled to an image processing unit 18 for processing the video signal on command from a control unit 20. The control unit 20 produces a video signal input command causing the image processing unit 18 to input the video signal from the camera 16. The image processing unit 18 processes the video signal for producing an image including a defective portion reflective of the light of diffused reflection if any. The control unit 20 estimates the surface condition of the transparent plate object O based on the defective portion of the produced image. The control unit 20 produces a display command causing the image processing unit 18 to display the produced image or the estimated result on a monitor 22. The control unit 20 also controls a light source control circuit 24 in a manner to alternatively actuate the first and second light sources 12 and 14 in synchronism with the video signal input command to the image processing unit 18.

The control unit 20 may employ a digital computer which includes a central processing unit (CPU), a random access memory (RAM), a read only memory (ROM), and an input/output control circuit (I/O). The central processing unit communicates with the rest of the computer via data bus. The read only memory contains the program for operating the central processing unit and further contains appropriate data used in estimating the surface condition of the transparent plate object O. A control word specifying an estimated surface condition is transferred by the central processing unit to the input/output control circuit for displaying the estimated result on the monitor 22.

FIG. 3 is a flow diagram of the programming of the digital computer used in the control unit 20. The computer program is entered at the point 202. At the point 204 in the program, a first command is produced, causing the light source control circuit 24 to disable the second light source 14 and to enable the first light source 12 so as to generate light from the first light source 12 in a direction toward the transparent plate object O. At the point 206 in the program, a video signal input command is produced, causing the image processing unit 18 to input a video signal from the camera 16.

Figure 4A:
FIGS. 4A-4E are diagrams used in explaining the operation of the image processing unit.
Figure 4B:

Following this, the video signal is processed in the image processing unit 18. Thus, at the point 208 in the program, the video signal is converted successively into a binary value of 1 or 0 representing a black or white pixel (picture element) to produce an image, as shown in FIG. 4A. At the point 210 in the program, the produced image is expanded in a direction determined by the direction of the light generated from the first light source 12; that is, the direction in which the light generated from the first light source 12 is incident on the transparent plate object O. With the dioptric system of FIG. 1, the produced image is expanded downward, as shown in FIG. 4B, when the generated light is obliquely downward incident on the transparent plate object O like this case. The produced image is expanded upward when the generated light is obliquely upward incident on the transparent plate object O, it is expanded rightward when the generated light is obliquely leftward incident on the transparent plate object O, as viewed from the side of the camera 16, and it is expanded leftward when the generated light is obliquely rightward incident on the transparent plate object O, as viewed from the side of the camera 16. At the point 212 in the program, the expanded image is stored in an image memory. It is to be appreciated that the produced image will include only a part of the circumference of the water droplet D, as shown in FIG. 4A, without such an expansion process.

The expansion process may be made by modifying or masking the produced image for each 3×3 matrix of pixels (A-I) of the produced image, as shown in FIG. 5. If the produced image is to be expanded downward like this case, the value of the center pixel (E) is set at 1 if any one of the values of the center pixel (E) and the pixels (A, B and C) located on the upper row of the matrix is 1. Otherwise, the value of the center pixel (E) is set at 0. If the produced image is to be expanded upward, the value of the center pixel (E) is set at 1 only when any one of the values of the center pixel (E) and the pixels (G, H and I) located on the lower row of the matrix is 1. If the produced image is to be expanded leftward, the value of the center pixel (E) is set at 1 only when any one of the values of the center pixel (E) and the pixels (C, F and I) on the right column of the matrix is 1. If the produced image is to be expanded rightward, the value of the center pixel (E) is set at 1 only when any one of the values of the center pixel (E) and the pixels (A, D and G) located on the left column of the matrix is 1.

At the point 214 in the program, a second command is produced, causing the light source control circuit 24 to disable the first light source 12 and to enable the second light source 14 to generate light from the second light source 14 in another direction toward the transparent plate object O. At the point 216 in the program, a video signal input command is produced, causing the image processing unit 18 to input a video signal from the camera 16.

Figure 4C:
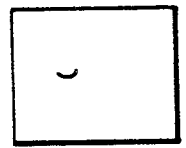
Figure 4D:

Following this, the video signal is processed in the image processing unit 18. Thus, at the point 218 in the program, the video signal is converted successively into a binary value of 1 or 0 representing a black or white pixel to produce an image, as shown in FIG. 4C. At the point 220 in the program, the produced image is expanded in a direction determined by the direction of the light generated from the second light source 14; that is, the direction in which the light generated from the second light source 14 is incident on the transparent plate object O. Since the generated light is obliquely upward incident on the transparent plate object O in this case, the produced image is expanded upward, as shown in FIG. 4D, in a manner similar to the process described previously in connection with the expansion step at the point 210. At the point 222 in the program, the expanded image is stored in an image memory.

Figure 4E:

At the point 224 in the program, the stored images are combined to produce a full image reflective of the water droplet D, as shown in FIG. 4E. At the point 226 in the program, the area of the image portion of the combined image corresponding to the water droplet(s) D is calculated for an estimation of the surface condition of the transparent plate object O. It is estimated that the amount of the water droplet(s) is great and the surface condition is not good when the calculated area is great. The estimated result is outputted at the point 228 in the program. Following this, the program proceeds to the end point 230.

Figure 6:
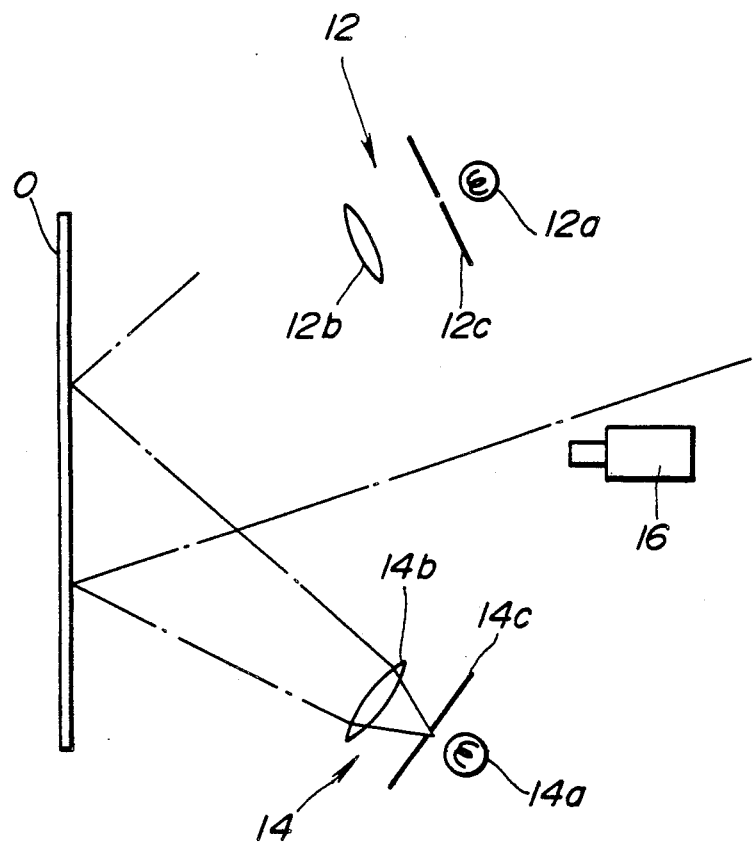
FIG. 6 is a schematic diagram showing a second embodiment of the invention.
Figure 7A:
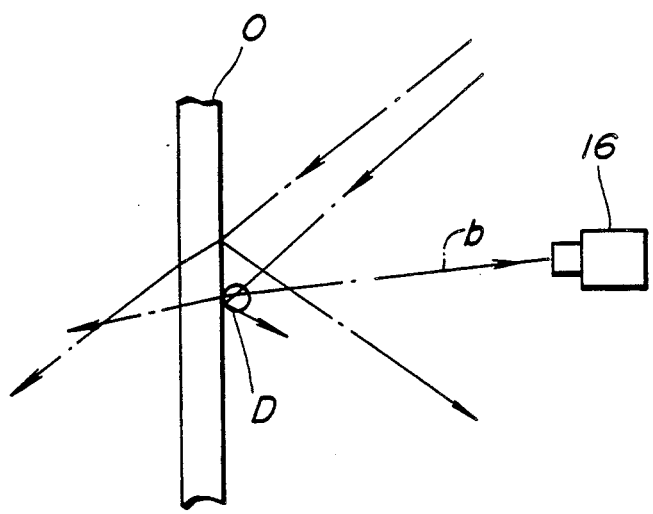
FIGS. 7A and 7B are diagrams used in explaining the light of diffused reflection from the transparent plate object.
Figure 7B:
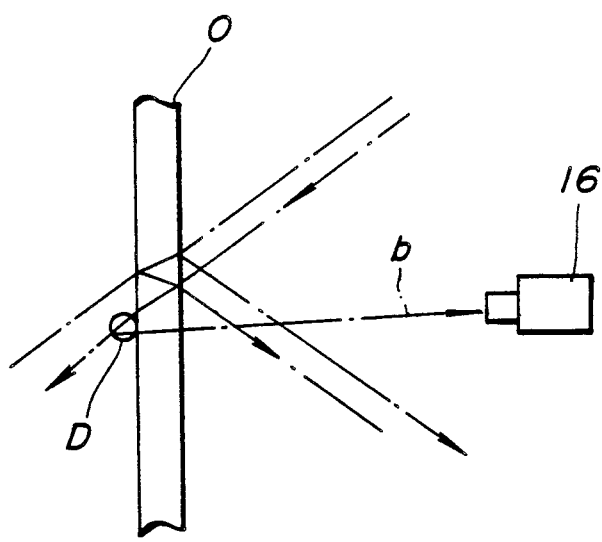

Referring to FIG. 6, there is shown a second embodiment of the invention which is generally the same as shown in FIG. 1 except that the lighting unit and the light sensor are located on the same side with respect to the transparent plate object O to form a catoptric system. Like reference numerals have been applied to FIG. 6 with respect to the equivalent components shown in FIG. 1. Also in this case, the camera 16 is located out of the optical paths of the light reflected from the transparent plate object O. The light generated from the first and second light sources 12 and 14 reflects on the transparent plate object O. When the transparent plate object O is complete, the camera 16 receives no light, as shown in FIG. 6. Assuming now that a water droplet D exists on either of the opposite surfaces of the transparent plate object O, as shown in FIGS. 7A and 7B, the camera 16 receives the light of diffused reflection on the water droplet D, as indicated by the phantom lines b of FIGS. 7A and 7B.

The operation of the second embodiment differs from that of the embodiment of FIG. 1 only in the direction of expansion of the produced image. In this embodiment, the produced image is expanded upward when the generated light is obliquely upward incident on the transparent plate object O, it is expanded downward when the generated light is obliquely downward incident on the transparent plate object O, it is expanded rightward when the generated light is obliquely rightward incident on the transparent plate object O, as viewed from the side of the camera 16, and it is expanded leftward when the generated light is obliquely leftward incident on the transparent plate object O, as viewed from the side of the camera 16.

It is to be appreciated that, with the second embodiment employing a catoptiric system, the object O to be tested is not limited in any way to transparent plates and may be a metal plate or other opaque plates.

Although the first and second embodiments have been described in connection with two light sources, it is to be appreciated that three or more light sources may be used to improve the estimation accuracy. In this case, it is preferable to actuate the light sources in a predetermined sequence in synchronism with the input command signal fed from the digital computer 20 to the image processing unit 18.

Figure 8:
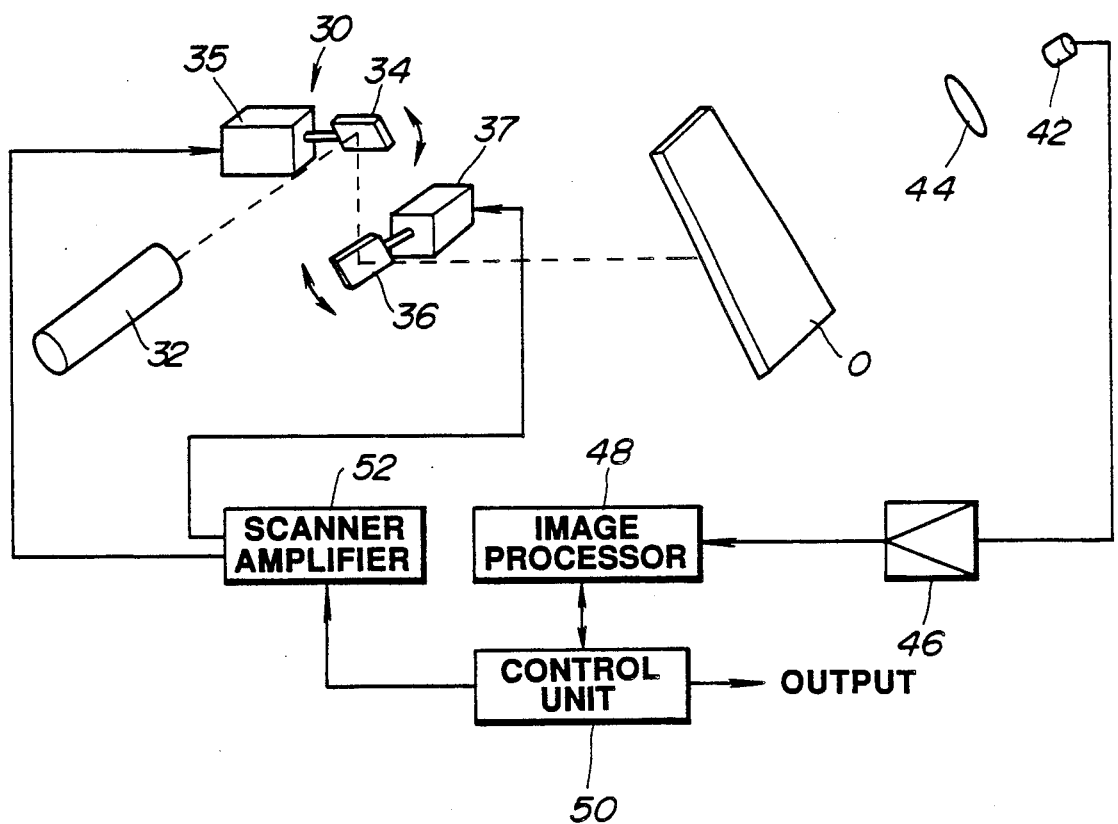
FIG. 8 is a schematic diagram showing a third embodiment of the invention.

Referring to FIG. 8, there is shown a third embodiment of the invention. In this embodiment, the lighting unit is taken in the form of a scanner 30 including a laser beam generator 32, and X and Y mirrors 34 and 36. A laser beam generated from the laser beam generator 32 is obliquely incident on the X mirror 34. The Y mirror 36 is positioned in the path of the incident beam reflected from the X mirror 34 to further reflect the reflected beam in a direction producing a light spot on the transparent plate object O. The light incident on the transparent plate object O passes through the transparent plate object O. In order to scan the whole area of the transparent plate object O, the scanner 30 also includes an X motor 35 for rotating the X mirror 34 to move the light spot in an X direction on the transparent plate object O, and a Y motor 37 for rotating the Y mirror 36 to move the light spot in a Y direction on the transparent plate object O.

A light sensor taken in the form of a photocell 42 is shown as located on the other side of the transparent plate object O remote from the scanner 30 and out of the path of the light passing through the transparent plate object O. A lens 44 is located in front of the photocell 42 to focus light thereon.

Figure 9:
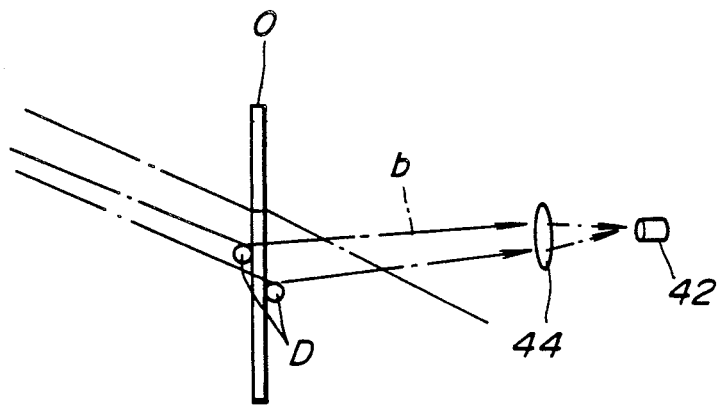
FIG. 9 is a diagram used in explaining the light of diffused reflection from the transparent plate object.

The light incident on the transparent plate object O passes through the transparent plate object O. When the transparent plate object O is complete, the photocell 42 receives no light, as show in FIG. 8. Assuming now that a water droplet D exists on one or both of opposite surfaces of the transparent plate object O, as shown in FIG. 9, the photocell 42 receives the light of diffused reflection on the water droplet D, as indicated by the phantom lines b of FIG. 9.

The photocell 42 converts the amplitude variations of the light impinging thereon into an electrical signal. The electrical signal is fed from the photocell 42 through an amplifier 46 to an image processing unit 48 for processing the input signal on command from a control unit 50. The control unit 50 also controls a scanner amplifier 52 to operate the X and Y motors 35 and 37.

The control unit 50 may employ a digital computer which includes a central processing unit (CPU), a random access memory (RAM), a read only memory (ROM), and an input/output control circuit (I/O). The central processing unit communicates with the rest of the computer via data bus. The read only memory contains the program for operating the central processing unit and further contains appropriate data used in estimating the surface condition of the transparent plate object O. A control word specifying an estimated surface condition is transferred by the central processing unit to the input/output control unit for outputting the estimated result to an output device such as a CRT display device, a printer, a floppy disc drive unit, and the like.

Figure 10:
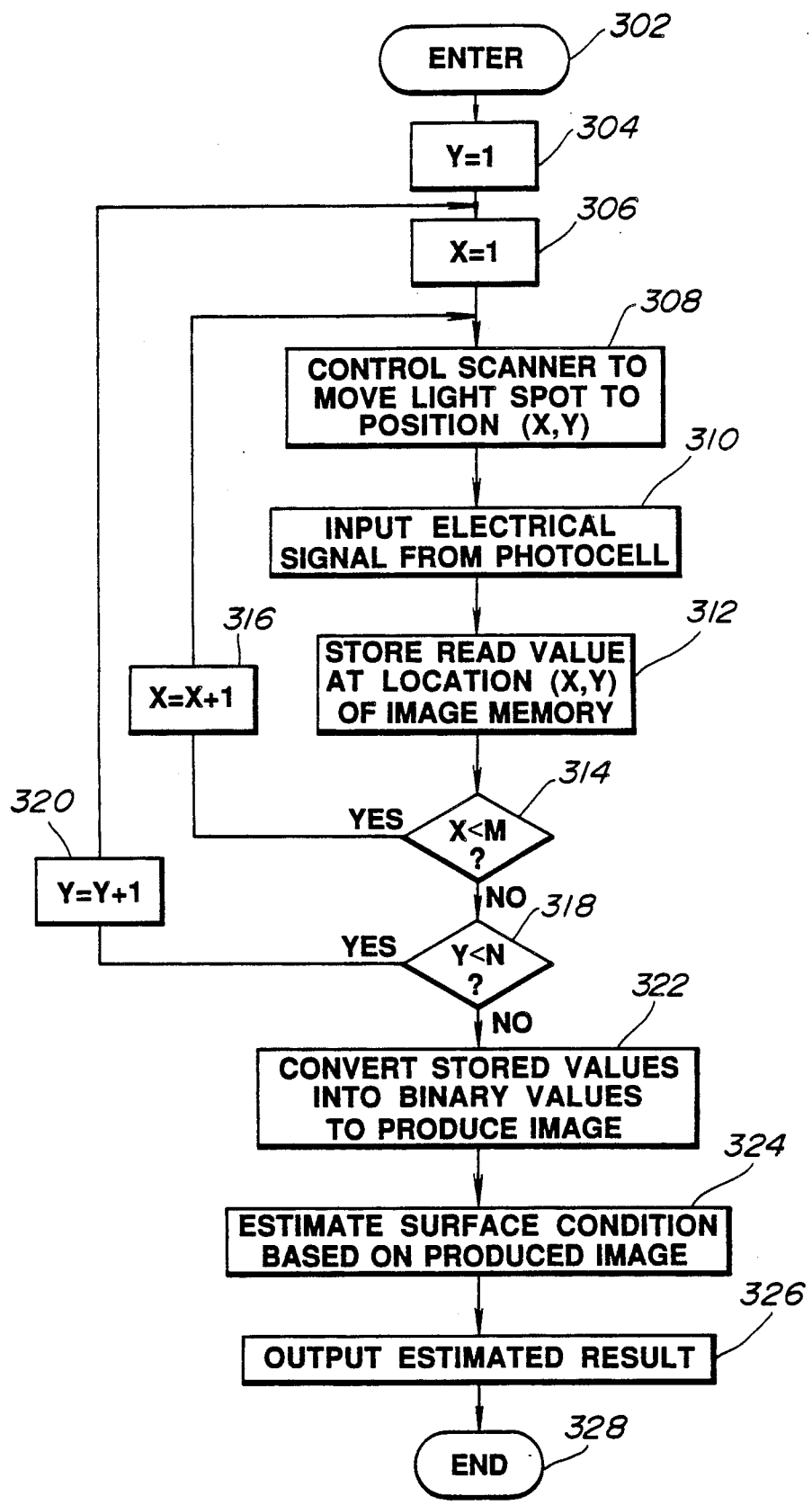
FIG. 10 is a flow diagram of the programming of the digital computer used in the apparatus of FIG. 8.
Figure 11A:
FIGS. 11A and 11B are diagrams used in explaining the operation of the image processing unit.

FIG. 10 is a flow diagram of the programming of the digital computer used in the control unit 50. The computer program is entered at the point 302. At the point 304 in the program, the Y counter is reset to its initial value $Y = 1$. At the point 306 in the program, the X counter is reset to its initial value X=1. At the point 308 in the program, a position command is outputted, causing the scanner amplifier 52 to drive the X and/or Y motors 35 and 37 in a manner to move the light spot to a commanded position (X, Y) on the transparent plate object O, this commanded position being represented by the coordinates (X, Y) corresponding to the counts X and Y of the X and Y counters. At the point 310 in the program, a signal input command is produced, causing the image processing unit 48 to input an electrical signal, as shown in FIG. 11A, fed thereto from the photocell 42. At the point 312 in the program, the magnitude value of the inputted electrical signal is stored in an image memory at a location (X, Y) assigned by the counts (X, Y) of the X and Y counters.

At the point 314 in the program, a determination is made as to whether or not the count X of the X counter is less than a maximum value M. If the answer to this question is "yes", then the program proceeds to the point 316 where the X counter is incremented by one step and then the program is returned to the point 308. If the answer to the question at the point 314 is "no", then it means that the light spot reaches the point at which the scanning operation along one scan line is terminated and the program proceeds to another determination step 318. This determination is as to whether or not the count Y of the Y counter is less than its maximum value N. If the answer to this question is "yes", then the program proceeds to the point 320 where the Y counter is incremented by one step and then the program is returned to the point 306. If the answer to the question at the point 318 is "no", then it means that the entire area of the transparent plate object O has been scanned and the program proceeds to the point 322.

Figure 11B:
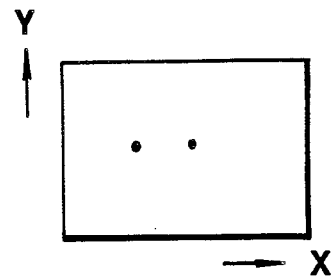

At the point 322 in the program, the values stored in the image memory are converted successively into a binary value of 1 or 0 representing a black or white pixel to produce an image, as shown in FIG. 11B. At the point 324 in the program, the area of the image portion corresponding to the water droplet(s) is calculated for an estimation of the surface condition of the transparent plate object O. It is estimated that the amount of the water droplet is great and the surface condition is not good when the calculated aera is great. At the point 326 in the program, the estimated result is outputted. Following this, the program proceeds to the end point 238.

Figure 12:
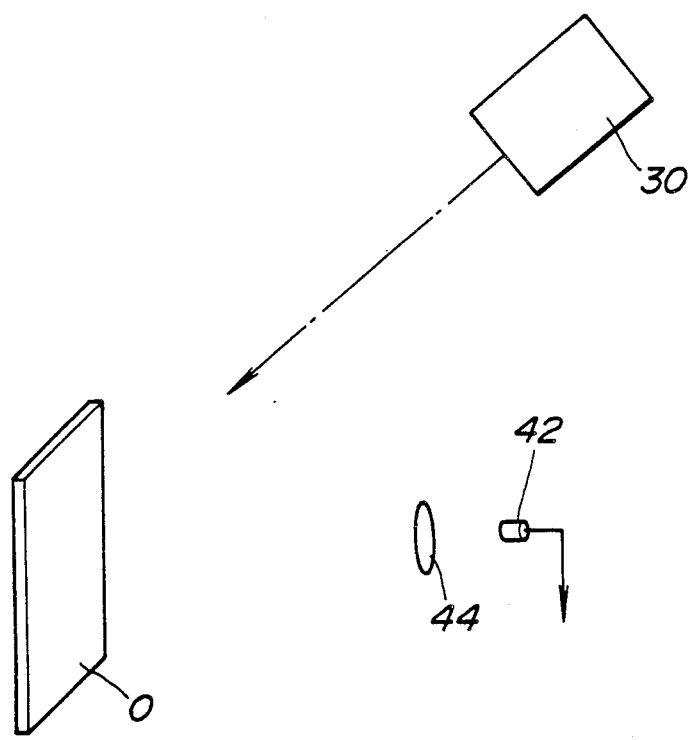
FIG. 12 is a schematic diagram showing a fourth embodiment of the invention.
Figure 13:
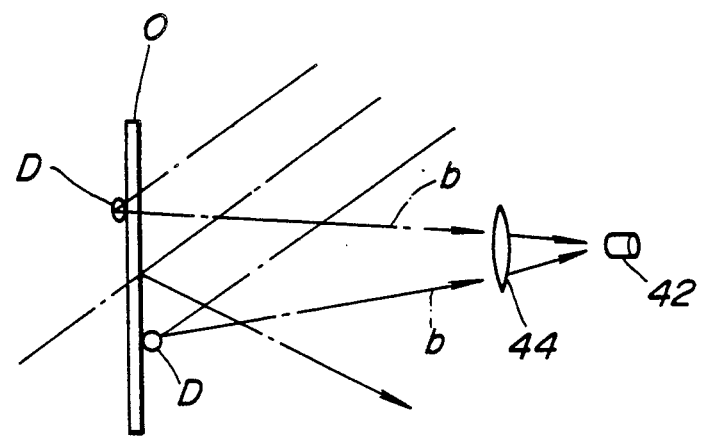
FIG. 13 is a diagram used in explaining the light of diffused reflection from the transparent plate object.

Referring to FIG. 12, there is shown a fourth embodiment of the invention which is generally the same as shown in FIG. 8 except that the lighting unit and the light sensor are located on the same side with respect to the transparent plate object O to form a catoptric system. Like reference numerals have been applied to FIG. 12 with respect to the equivalent components shown in FIG. 8. Also in this case, the photocell 42 is located out of the optical paths of the light reflected from the transparent plate object O. The laser beam generated from the laser scanner 30 reflects on the transparent plate object O. When the transparent plate object O is complete, the photocell 42 receives no light, as shown in FIG. 13. Assuming now that water droplets D exists on both of the opposite surfaces of the transparent plate object O, as shown in FIG. 13, the photocell 42 receives the light of diffused reflection from the water droplets D, as indicated by the phantom lines b of FIG. 13. The remainder of the circuits are the same as described for the third embodiment of FIG. 8, hence a detailed description will be omitted to avoid duplicity.

It is to be appreciated that, with the fourth embodiment employing a catoptiric system, the object O to be tested is not limited in any way to transparent plates and may be a metal plate or other opaque plates.

Figure 14:
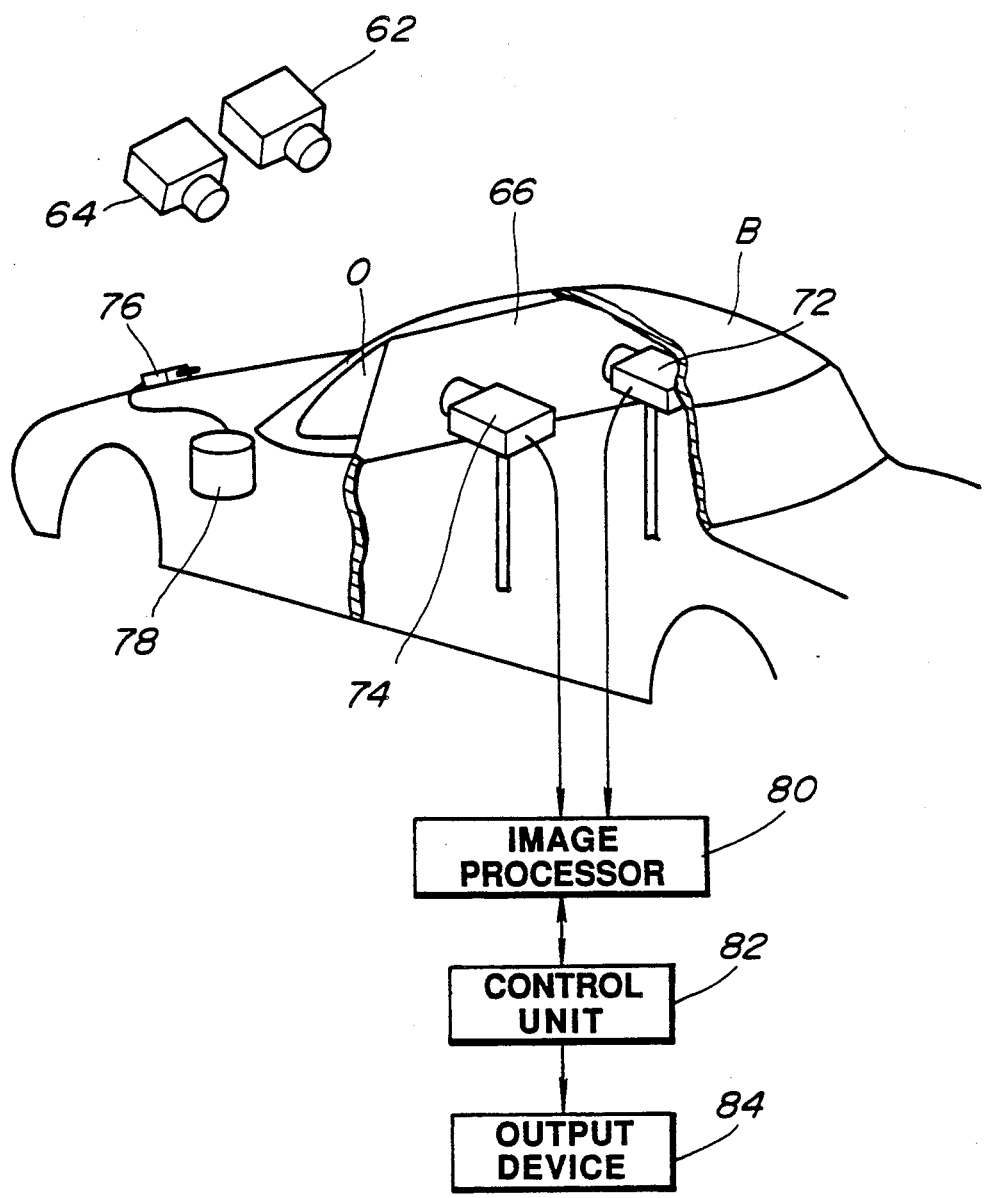
FIG. 14 is a schematic diagram showing a fifth embodiment of the invention.

Referring to FIG. 14, there is shown a fifth embodiment of the invention applied to estimate the performance or efficiency of a wind-shield wiper provided for wiping a front wind-shield glass plate O fixed on an automotive vehicle body B. In this embodiment, the lighting unit is shown as including two light sources 62 and 64 located in front of the wind-shield glass plate O for generating light to project an image on a screen 66 provided in the rear of the wind-shield glass plate O. The projected image is reflective of the surface condition of the wind-shield glass plate O. The first light source 62 is used to illuminate the right portion of the wind-shield glass plate O on the side of the driver's seat. The second light source 64 is used to illuminate the left portion of the wind-shield glass plate O on the side of the assistant driver's seat.

Figure 15:
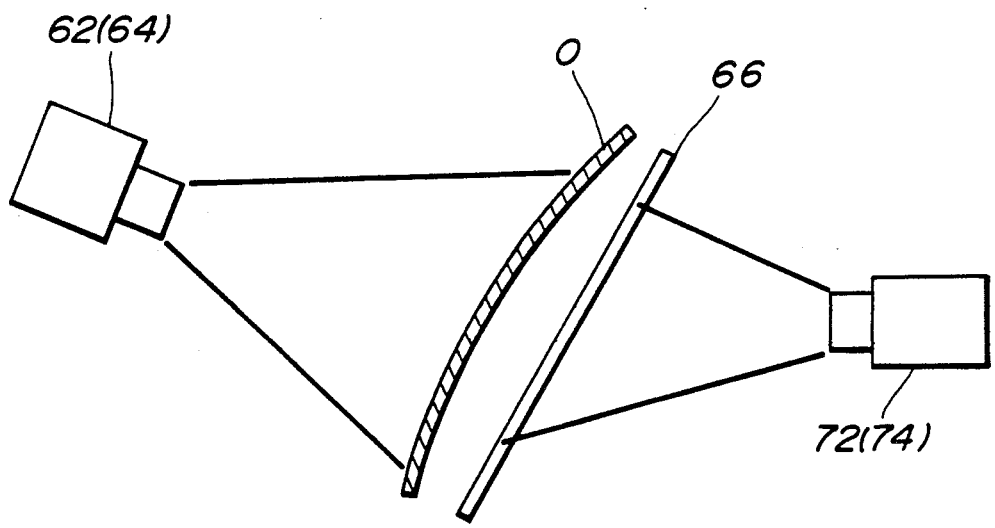
FIG. 15 is a diagram showing the position of one of the cameras with respect to the corresponding one of the light sources.

The light sensor is shown as including two television cameras 72 and 74 located for observing the image projected on the screen 66. The first camera 72 is used for observing the right portion of the projected image on the side of the driver's seat. The second camera 74 is used for observing the left portion of the projected image on the side of the assistant driver's seat. The position of one of the cameras relative to the corresponding light source is best shown in FIG. 15.

An ejector 76 is mounted on the vehicle body B at a position suitable for ejecting water under pressure in the form of a spray against the wind-shield glass plate O. The numeral 78 designates a water tank from which water is supplied to the ejector 76. After the actuation of the ejector 76, an unshown wind-shield wiper is operated to wipe the wind-shield glass surface. Each of the first and second cameras 72 and 74 converts brightness variations on the corresponding one of the right and left portions of the image projected on the screen 60 into an electrical signal. The electrical signal is inputted to an image processing unit 80 on command from a control unit 82 in synchronism with the operation of the wind-shield wiper for estimating the condition of the wiped surface of the wind-shield glass plate O. The estimated result is outputted to an output device 84 such as a CRT display unit, a printer, a floppy disc drive unit, or the like.

The control unit 82 may employ a digital computer which includes a central processing unit (CPU), a random access memory (RAM), a read only memory (ROM), and an input/output control circuit (I/O). The central processing unit communicates with the rest of the computer via data bus. The input/output control circuit includes an analog-to-digital converter which receives analog signals from the first and second cameras 72 and 74 and converts them into digital form for application to the central processing unit. The A to D conversion process is initiated on command from the central processing unit which selects the input channel to be converted. The read only memory contains the program for operating the central processing unit and further contains appropriate data used in estimating the surface condition of the wind-shield glass plate O. A control word specifying an estimated surface condition is transferred by the central processing unit to the input-/output control unit for outputting the estimated result to the output device 84.

FIG. 16 is a flow diagram of the programming of the digital computer used in the control unit 82. The computer program is entered at the point 402 in synchronism with the operation of the wind-shield wiper. Following this, the electrical signals from the first and second cameras 72 and 74 are, one by one, inputted through the analog-to-digital converter into the image processing unit 80. Thus, at the point 404 in the program, the electrical signal from the first camera 72 is converted into digital form and read into a first image memory. Similarly, at the point 406, the electrical signal from the second camera 74 is converted into digital form and read into a second image memory.

Figures 17, 18A, 18B:
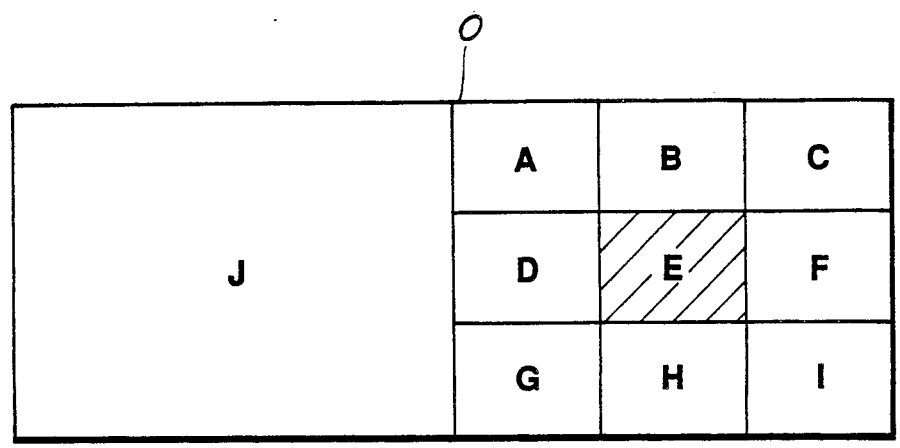
FIG. 17 is a diagram used in explaining memory sections into which the image memory is divided.
FIGS. 18A and 18B are diagrams of spatial filters which may be used in the fifth embodiment.

The first image memory is divided into a plurality of (in the illustrated case 3×3) sections storing digital values for the respective segments A, B, C, D, E, F, G, H and I of the full image projected on the right portion of the screen 66, as shown on the right side of FIG. 17. It is now assumed that the center image segment E includes the driver's eye point. The second image memory is used for storing a digital value for the full image J projected on the left portion of the screen 66 on the side of the assistant driver, as shown on the left side of FIG. 17. It is to be appreciated, of course, that the number of the divided memory section is not limited to the illustrated case. In addition, it is to be appreciated that the first and second image memories may be replaced by a single image memory divided into a plurality of (in the illustrated case 1 plus 3×3) memory sections.

At the point 408 in the program, each of the stored digital values $P(x,y)$ is modified using spatial filters adapted to produce an absolute value of the difference between the maximum and minimum values thereof in order to emphasize the water lines left on the surface of the wind-shield glass plate O. This filtering process may be replaced by a well-known edge detecting process using a longitudinal line detecting spatial filter as shown in FIG. 18A and a transverse line detecting spatial filter as shown in FIG. 18B. At the point 410 in the program, each of the modified digital values $Q(x,y)$ is converted into a binary value of 1 or 0 representing a black or white pixel to produce an image reflective of the water lines left on the surface of the wind-shield glass plate O. At the point 412 in the program, a first group of parameters A1, B1, C1, D1, E1, F1, G1, H1, I1 and J1 indicative of the areas of the water lines appearing on the respective image segments A, B, C, D, E, F, G, H, I and J are calculated. At the point 414 in the program, the calculated parameters A1 to J1 are stored in the computer memory.

At the point 416 in the program, the digital values $P(x,y)$ read at the points 404 and 406 are combined with the corresponding digital values $Q(x,y)$ modified at the point 408 as $Q(x,y)-P(x,y)+k$ where k is a constant. This is effective to emphasize the water films left on the surface of the wind-shield glass plate O. At the point 418 in the program, each of the combined digital values is converted into a binary value of 1 or 0 representing a black or white pixel to produce an image reflective of the water films left on the surface of the wind-shield glass plate O. At the point 420 in the program, a second group of parameters A2, B2, C2, D2, E2, F2, G2, H2, I2 and J2 indicative of the areas of the water films appearing on the respective image segments A, B, C, D, E, F, G, H, I and J are calculated. At the point 422 in the program, the calculated parameters A2 to J2 are stored in the computer memory.

At the point 424 in the program, the surface condition of the wind-shield glass plate O is estimated as $S=(1/K1)\{a(A1+A2)+a(B1+B2)+a(C1+C2)+a(D1+D2)+b(E1+E2)+a(F1+F2)+a(G1+G2)+a(H1+H2)+a(I1+I2)\}+(1/K2)\{a(J1+J2)\}$ where K1 and K2 are normalizing coefficients and a and b are weighting coefficients. The weighting constant b is set at a value greater than the weighting coefficient b in order to provide a greater weight on the segment including the driver's eye point. The estimated result S is outputted to the output unit at the point 426. Following this, the program proceeds to the end point 428.

It is preferable to determine the weighting coefficients a and b in such a manner that the estimated result S has a good mutual relation to the result of human estimation.

Although two cameras 72 and 74 are used to cover the entire area of the wind-shield glass plate surface, it is to be appreciated that one or more camera may be used to cover the entire or partial area of the wind-shield glass plate surface. In addition, plate objects which can be tested in this embodiment are not limited to the wind-shield glass plate.

What is claimed is:

1. An apparatus for estimating a surface condition of a plate object, comprising:
   a lighting unit for generating light toward the plate object, the lighting unit including a plurality of light sources for generating light in different directions toward the plate object;
   means for controlling the light unit to cause sequential actuation of the light sources in a predetermined sequence;
   a light sensor located out of paths of the light generated from the lighting unit for producing an electrical signal in response to light of diffused reflection from the plate object;
   a processing unit for processing the electrical signal fed thereto from the light sensor for producing an image including a defective portion reflective of the light of diffused reflection, the processing unit including means for storing an image segment produced during the actuation of each of the light sources, means for expanding the image segment in a direction determined by the direction of the light incident on the plate object, and means for combining all of the expanded image segments to produce the image; and
   an estimating unit for estimating the surface condition of the plate object based on the defective portion of the produced image.

2. The apparatus as claimed in claim 1 wherein the estimating unit includes means for calculating an area of the defective portion of the produced image, and means for estimating the surface condition of the plate object based on the calculated area of the defective portion of the produced image.

3. The apparatus as claimed in claim 2 wherein the lighting unit and the light source are located on the opposite sides with respect to the plate object.

4. The apparatus as claimed in claim 2, wherein the lighting unit and the light source are located on the same side with respect to the plate object.

5. The apparatus as claimed in claim 1, wherein the light sensor includes a television camera located out of paths of the light generated from the lighting unit for producing a video signal.

6. The apparatus as claimed in claim 1, wherein the lighting unit includes a photocell located out of paths of the light generated from the lighting unit for converting amplutude variations of the light impinging thereon into an electrical signal.

7. The apparatus as claimed in claim 6, wherein the light source includes a scanner employing a laser beam for scanning the plate object.

8. The apparatus as claimed in claim 7, wherein the photocell and the scanner are located on the opposite sides with respect to the plate object.

9. The apparatus as claimed in claim 7, wherein the photocell and the scanner are located on the same side with respect to the plate object.

10. An apparatus for estimating a surface condition of a plate object, comprising:
 a lighting unit for generating light toward the plate object;
 a light sensor for converting brightness variations of the light impinging on the plate object into an electrical signal;
 a processing unit for processing the electrical signal fed thereto from the light sensor for producing a plurality of image segments forming a full image of the surface of the plate object; and
 an estimating unit for estimating the surface condition of the plate object based on a defective portion included in each of the image segments, the estimating unit including means for providing a heavier weight on a defective portion of at least one of the image segments than that of the other image segments.

11. The apparatus as claimed in claim 10, wherein the estimating unit includes means for calculating an area of the defective portion of each of the image segments, means for weighting the calculated area of the defective portion of the one image segment heavier than that of the other image segments, and means for estimating the surface condition of the plate object based on the weighted areas.

12. The apparatus as claimed in claim 10, wherein the lighting unit includes at least one light source for generating light toward the plate object to project an image on a screen, the projected image being reflective of the surface condition of the plate object, and wherein the light sensor includes at least one camera located for observing the image projected on the screen to convert the projected image into the electrical signal.

13. An apparatus for estimating an efficiency of a wind-shield wiper provided for wiping a surface of a wind-shield glass plate, comprising:
 a lighting unit for generating light toward the wind-shield glass plate;
 a light sensor for converting brightness variations of the light impinging on the wind-shield glass plate into an electrical signal;
 a processing unit for processing the electrical signal fed thereto from the light sensor for producing a plurality of image segments forming a full image of the surface of the wind-shield glass plate; and
 an estimating unit for estimating the efficiency of the wind-shield wiper based on a defective portion included in each of the image segments, the estimating unit including means for providing a heavier weight on a defective portion of at least one of the image segments than that of the other image segments.

14. The apparatus as claimed in claim 13, wherein the one image segment corresponds a wind-shield glass plate portion including a driver's eye point.

15. The apparatus as claimed in claim 13 wherein the estimating unit includes means for calculating an area of the defective portion of each of the image segments, means for weighting the calculated area of the defective portion of the one image segment heavier than that of the other image segments, and means for estimating the efficiency of the wind-shield wiper based on the weighted areas.

16. The apparatus as claimed in claim 13, wherein the estimating unit includes means for estimating the efficiency of the wind-shield wiper based on a first defective portion reflective of water lines left on the wind-shield glass plate surface and a second defective portion reflective of water films left on the wind-shield glass plate.

17. The apparatus as claimed in claim 16, wherein the estimating unit includes means for calculating a first area of the first defective portion of each of the image segments, means for weighting the calculated first area of the first defective portion of the one image segment heavier than that of the other image segments, means for calculating a second area of the second defective portion of each of the image segments, means for weighting the calculated second area of the defective portion of the one image segment heavier than that of the other image segments, and means for estimating the efficiency of the wind-shield wiper based on the weighted first and second areas.

18. The apparatus as claimed in claim 17, wherein the one image segment corresponds to a wind-shield glass plate portion including a driver's eye point.

19. The apparatus as claimed in claim 13, wherein the lighting unit includes at least one light source for generating light toward the wind-shield glass plate to project an image on a screen, the projected image being reflective of a condition of the surface of the wind-shield glass plate, and wherein the light sensor includes at least one camera located for observing the image projected on the screen to convert the projected image into the electrical signal.

* * * * *